United States Patent [19]

Featherstone

[11] 4,407,703

[45] Oct. 4, 1983

[54] AMINE SEPARATION PROCESS

[75] Inventor: William Featherstone, Nunthorpe, England

[73] Assignee: Imperial Chemical Industries PLC, London, England

[21] Appl. No.: 349,816

[22] Filed: Feb. 18, 1982

Related U.S. Application Data

[63] Continuation of Ser. No. 227,344, Jan. 22, 1981, abandoned.

[30] Foreign Application Priority Data

Feb. 8, 1980 [GB] United Kingdom ............... 804303

[51] Int. Cl.³ .................... B01D 3/14; B01D 11/04
[52] U.S. Cl. ................... 203/43; 564/497; 564/499
[58] Field of Search ............. 203/43, 19; 564/497, 564/499

[56] References Cited

U.S. PATENT DOCUMENTS 3,433,788 3/1969 Somekh et al. ............... 564/497

Primary Examiner—Frank Sever
Attorney, Agent, or Firm—Cushman, Darby & Cushman

[57] ABSTRACT

A mixture of isomers of an alkylamine, for example ethylamine is separated into its constituent components by a process in which the mixture is first distilled and at least one pure component separated from the mixture. The remainder of the mixture is then subjected to a multi-stage liquid-liquid extraction, preferably in five theoretical stages using water as extractant. For example, in the separation of mixtures of ethylamines, substantially all of the mono-ethylamine and a large proportion of the di-ethylamine is recovered in the distillation stage. The use of a multi-stage extraction (instead of the more usual single-stage extraction) to treat the remainder of the mixture leads to an enhanced yield of tri-ethylamine and lower consumption of energy and of extractant.

3 Claims, 1 Drawing Figure

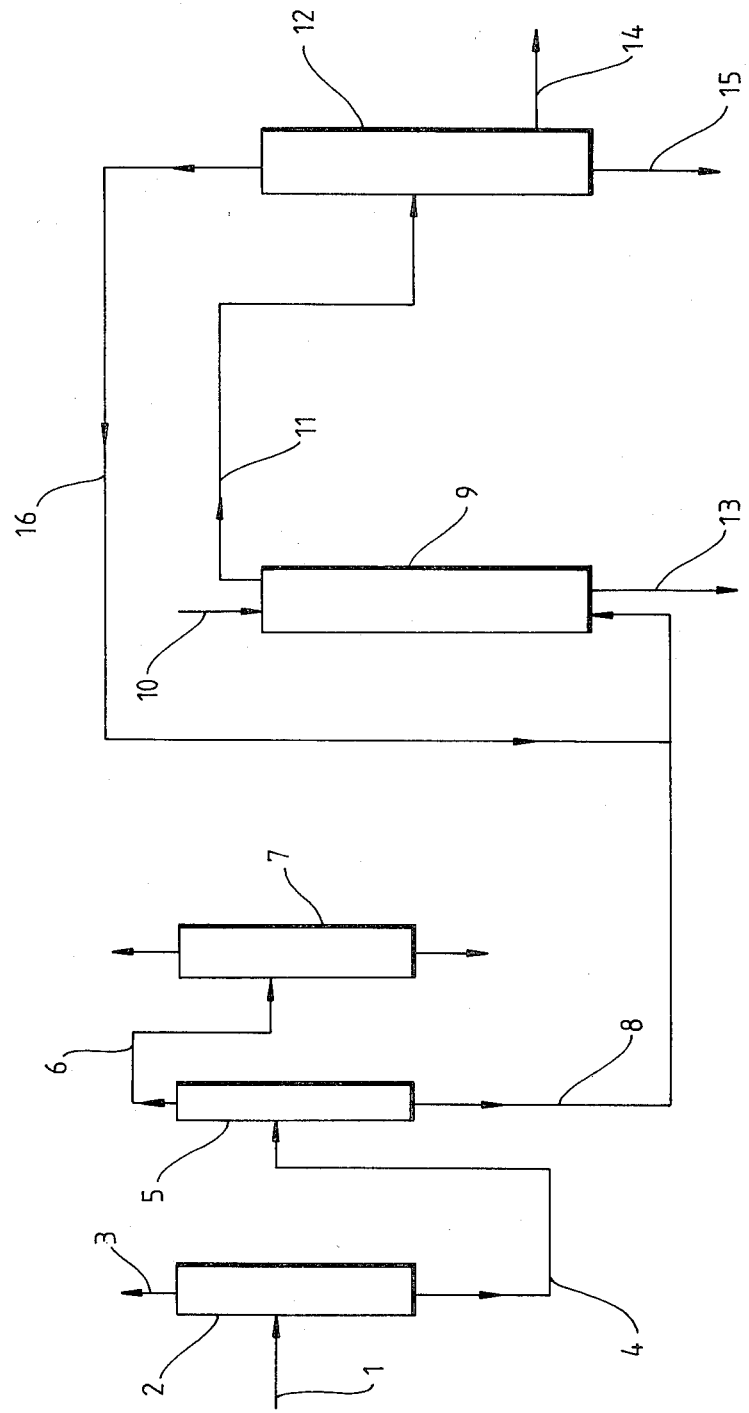

AMINE SEPARATION PROCESS

This is a continuation of application Ser. No. 227,344 filed Jan. 22, 1981, now abandoned.

The present invention relates to the separation of amines, in particular to the separation of ethylamines and higher amines.

A commonly used method for the production of amines is by reaction of the corresponding alcohol with ammonia over a suitable amination catalyst, for example nickel or copper. For example, in the case of ethylamines manufacture, ethanol is reacted with ammonia and the product of the process is a mixture of unreacted ethanol and ammonia together with mono-, di- and tri-ethylamines and co-product water. The product of other amines leads to correspondingly similar product mixtures. The components of the product mixture may be separated by distillation but for most amine product mixtures, difficulties arise because of the closeness of boiling point of some components and/or because of azeotrope formation. For example, in the case of ethylamines the ammonia in the product mixture is readily separable by distillation but separation of the other components is less easy. Various proposals have been made involving various combinations of distillation, extraction and recycle steps and good separations of the various components have been achieved. However none of the separation systems is wholly ideal and so amines plant operators are continually striving to improve and simplify the separation systems. Moreover, the use of multi-distillation trains, extraction steps and recycle of various streams means that energy and materials costs are significant factors in the economics of these processes. Reductions in such costs as well as improvements in the effectiveness of separation of the various components of the amine product mixture are thus highly desirable.

Referring again to ethylamines manufacture as a typical example, one method of separating the components of the product mixture has involved, firstly, a series of distillation steps in which all of the ammonia, all of the mono-ethylamine and a large proportion of the diethylamine are separated from the mixture and from each other. The remainder of the mixture comprising the rest of the di-ethylamine, the tri-ethylamine, ethanol and water is subjected to a one-stage liquid-liquid extraction with added water at a temperature of about 65° C. The aqueous phase resulting from this extraction contains the ethanol, the di-ethylamine and a minor proportion of the triethylamine. The organic phase contains a major proportion of the tri-ethylamine, together with some water, ethanol and diethylamine. The organic phase is then distilled to yield a sidestream of pure triethylamine. The other components, apart from a small amount of heavy ends, are removed overhead but the principal component of the overhead fraction is still triethylamine. This fraction is recycled. The recovery of triethylamine in this process is clearly not ideal but we have now surprisingly found that a simple modification to this amines separation process improves both the yield of amine product and reduces the consumption of energy.

According to the present invention a process of separating a mixture comprising isomers of an alkylamine comprises distilling the mixture in one or more stages to separate at least one pure component of the mixture and subjecting the remainder of the thus distilled mixture to a multi-stage liquid-liquid extraction to yield an extract rich in at least one other component of the mixture.

The applicants have found that the use of a multi-stage liquid extraction step to replace the conventional one-stage extraction leads to higher recovery of desired amine at a lower energy usage per tonne amine produced.

Preferably, the mixture comprises a mixture of ethylamines and the multi-stage liquid-liquid extraction consists of two theoretical stages, more preferably five theoretical stages, using water as the extractant. Preferably the mixture of ethylamines fed to the multi-stage extraction step comprises a mixture of diethylamine, triethylamine, water and ethanol, the ammonia and monoethylamine present in the initial product mixture having been removed by the distillation stage(s). In the multi-stage extraction step, the water extracts the ethanol and diethylamine from the mixture.

A suitable temperature of operation for the multi-stage extraction step is similar to that used for the conventional one-stage extraction step; that is in the range 60° to 70° C., say about 65° C. but in a preferred form of the process of this invention the multi-stage extraction step is operated at a higher temperature, suitably in the range 75° C. to 95° C. Use of this higher range of temperature necessitates operation at modestly elevated pressures, say of the order of 2 bars, rather than atmospheric pressure (which is used in the conventional one stage process at lower temperatures). The Applicants have found that operation at the higher temperature range increases the yield of triethylamine from the process.

The multi-stage extraction step of the process of this invention is conveniently carried out in a multi-stage extraction column, preferably one containing the equivalent of five theoretical stages and in which the extractant is contacted countercurrently with the mixture of amines, for example an agitated column system such as a rotating disc contactor or a Kuhni extractor. Alternatively, the extraction may be carried out in other equipment, for example a bank of mixer-settler units.

The amine mixture fed to the multi-stage extraction step may, depending on its temperature, be a single phase to two phase mixture, the latter comprising amine and aqueous phases. If the mixture is two-phase, it may be fed in its entirety to the multi-stage extraction or a preliminary separation of the phases may be effected and only the amine phase passed to the extraction step. The aqueous phase is sent for further treatment, for example stripping, to recover its components.

The process of this invention is also useful in separating mixtures of other amines, for example iso-propylamines in which the yield of di-iso-propylamine is enhanced by use of the process of this invention again using water as the liquid extractant. For isopropylamine separation, the optimum number of theoretical stages is believed to be five and in addition to the increased yield of di-iso-propylamine there is some saving in energy compared with prior art conventional processes.

One embodiment of the invention is hereinafter described in more detail with reference to the accompanying diagram which is a flow diagram of one embodiment of the present invention.

Referring to the drawing, a product mixture from an ethylamines manufacturing process was fed along line 1 to distillation column 2. The components of the product mixture comprised ammonia, mono-, di- and tri-ethylamines, ethanol and water. In distillation column 2 all the ammonia in the mixture together with minor amounts of water and mono-ethylamine was removed overhead along line 3. The remainder of the mixture was removed as bottoms along line 4 and passed to a second distillation column 5 from which all the remaining monoethylamine together with a large proportion of the diethylamine was removed overhead along line 6. This overhead fraction was separated in a third distillation column 7 into monethylamine, removed overhead, and diethylamine, removed as bottoms.

The bottoms product from column 5 comprising principally triethylamine and water together with relatively smaller amounts of diethylamine and ethanol was removed along line 8 toward a multi-stage extractor 9 having the equivalent of five theoretical stages. Water for the extraction was fed from line 10. The extractor 9 was operated at a suitable temperature, for example 65° C., and from the last stage a product rich in triethylamine but still containing small amounts of diethylamine, water and ethanol was fed along line 11 to distillation column 12. The aqueous phase from the extractor was removed along line 13 for further treatment to recover di- and triethylamine and ethanol. In column 12 the triethylamine-rich phase from the extractor was distilled and pure triethylamine removed as a side stream along line 14. Heavy ends were removed along line 15 and the overhead fraction comprising principally triethylamine with some diethylamine, ethanol and water was recycled along line 16 to the extractor 9.

A comparative experiment illustrates the improvement effected by the process of this invention over the conventional one-stage process. In this experiment the bottoms product from column 5 had a composition of 8.0% diethylamine, 29.7% triethylamine, 7.9% ethanol and 54.4% water. When subjected to a conventional single-stage extraction with water 57% of the triethylamine contained in the reaction mixture originally fed to column 2 along line 1 was recovered. However, subjecting the same reaction mixture to a multi-stage extraction according to the process of this invention in an extraction column having 5 stages resulted in 81% of the triethylamine in the reaction mixture being recovered if the extraction was carried out at 65° C. Moreover, the amount of water required in the multi-stage extraction was less than 50% of that required in the one-stage extraction. Increasing the temperature of extraction in the multi-stage extraction to 90° C. resulted in 87% of the triethylamine being recovered.

The process of the invention therefore results in a greater yield of triethylamine with much less extractant used than in the single-stage conventional process. The consumption of energy is also appreciably lower than in the conventional process since smaller volumes of the various process streams require to be handled.

I claim:

1. A process of separating a mixture comprising ammonia, mono-, di-, and tri-ethylamines, ethanol and water which comprises distilling the mixture in one or more stages to separate from said mixture substantially all the ammonia and mono-ethylamine and at least some of the ethanol and di-ethylamine, and subjecting the remainder of the thus distilled mixture comprising di-ethylamine, triethylamine, water and ethanol to a multi-stage liquid-liquid extraction using water as the sole extractant, said multi-stage extraction being carried out at a temperature in the range 75° to 95° C. and at a pressure greater than atmospheric pressure, recovering from said multi-stage extraction an aqueous extract rich in triethylamine and containing small amounts of diethylamine, water and ethanol and distilling said extract to recover pure triethylamine as the distillate, the process being characterized by reduced energy consumption and by increased recovery of triethylamine using less water extractant than when a single stage extraction is employed.

2. A process as claimed in claim 1 in which the multi-stage liquid extraction consists of two theoretical stages.

3. A process as claimed in claim 1 in which the multi-stage liquid extraction consists of five theoretical stages.

* * * * *